(12) United States Patent
Diehn et al.

(10) Patent No.: US 11,959,085 B2
(45) Date of Patent: Apr. 16, 2024

(54) REGULATORY ELEMENTS FROM LAMIUM LEAF DISTORTION ASSOCIATED VIRUS (LLDAV)

(71) Applicants: PIONEER HI-BRED INTERNATIONAL, INC., Johnston, IA (US); CORTEVA AGRISCIENCE LLC, Indianapolis, IN (US)

(72) Inventors: Scott Diehn, West Des Moines, IA (US); Michelle Van Allen, Urbandale, IA (US); Albert L Lu, West Des Moines, IA (US)

(73) Assignees: PIONEER HI-BRED INTERNATIONAL, INC., Johnston, IA (US); CORTEVA AGRISCIENCE LLC, Indianapolis, IN (US)

( * ) Notice: Subject to any disclaimer, the term of this patent is extended or adjusted under 35 U.S.C. 154(b) by 337 days.

(21) Appl. No.: 16/797,472

(22) Filed: Feb. 21, 2020

(65) Prior Publication Data
US 2020/0181630 A1   Jun. 11, 2020

Related U.S. Application Data

(63) Continuation of application No. 15/502,129, filed as application No. PCT/US2015/042842 on Jul. 30, 2015, now abandoned.

(60) Provisional application No. 62/034,970, filed on Aug. 8, 2014.

(51) Int. Cl.
*C12N 15/82* (2006.01)

(52) U.S. Cl.
CPC ..... *C12N 15/8216* (2013.01); *C12N 15/8222* (2013.01); *C12N 2730/00022* (2013.01); *C12N 2730/00043* (2013.01)

(58) Field of Classification Search
None
See application file for complete search history.

(56) References Cited

U.S. PATENT DOCUMENTS

| | | | |
|---|---|---|---|
| 5,994,521 A * | 11/1999 | Maiti | C12N 15/8216 536/23.6 |
| 7,166,465 B2 * | 1/2007 | Thomas | C07K 14/415 800/320.2 |
| 2012/0167249 A1 | 6/2012 | Diehn et al. | |
| 2017/0226525 A1 | 8/2017 | Diehn et al. | |

FOREIGN PATENT DOCUMENTS

WO   2012088227 A1   6/2012

OTHER PUBLICATIONS

Zhang et al. Lamium leaf distortion associated virus, complete genome. (2008) GenBank Accession EU554423; pp. 1-4 (Year: 208).*
Llorens et al. Caulimoviridae (2010) Nucleic Acids Research; vol. 39; Suppl.1; D70-D74; pp. 1-4; published online at http://gydb.org/index.php/Caulimoviridae) (Year: 2010).*
Zhang et al. Studies on biology and genomic characterization of a caulimo-like virus associated with a leaf distortion disease of Lamium maculatum. (2008) Arch. Virol.; vol. 153; pp. 1181-1184 (Year: 2008).*
Koia et al. Pineapple translation factor SUI1 and ribosomal protein L36 promoters drive constitutive transgene expression patterns in *Arabidopsis thaliana*. (2013) Plant Molecular Biology; vol. 81; pp. 327-336 (Year: 2013).*
Mitsuhara et al. Efficient promoter cassettes for enhanced expression of foreign genes in dicotyledonous and monocotyledonous plants. (1996) Plant Cell Physiology; vol. 37; pp. 49-59 (Year: 1996).*
Bilas et al. Cis-regulatory elements used to control gene expression in plants. (2016) Plant Cell Tiss. Organ Cult.; vol. 127; pp. 269-287 (Year: 2016).*
EBI Accession No. EU554423 ; "Lamium leaf distortion associated virus, complete genome." (2008).
Zhang et al; "Studies on biology and genomic characterization of a caulimo-like virus associated with a leaf distortion disease of Lamium maculatum", Archives of Virology, vol. 153: 1181-1184 (2008).
Stavolone et al; "Cestrum yellow leaf curling virus (CmYLCV) promoter for heterologous gene expression in a wide variety of crops", Plant Molecular Biology, vol. 53(5): 703-713 (2003).
Zhang et al (Arch. Viral. (2008) vol. 153; pp. 1181-1184 (Year: 2008).
The International Search Report and Written Opinion for International Application No. PCT/US2015/042842 dated Oct. 28, 2015.
International Preliminary Report on Patentability for International Application No. PCT/US2015/042842, dated Feb. 23, 2017, 8 Pages.
Odell J.T., et al., "Identification of DNA Sequences Required for Activity of the Cauliflower Mosaic Virus 35S Promoter," Nature, 1985, vol. 313, pp. 810-812.

* cited by examiner

*Primary Examiner* — Cathy Kingdon Worley

(57) ABSTRACT

The present disclosure provides compositions and methods for regulating expression of heterologous nucleotide sequences in a plant. Compositions include a novel nucleotide sequence for regulatory elements from Lamium Leaf Distortion Associated Virus. A method for expressing a heterologous nucleotide sequence in a plant using the regulatory element sequences disclosed herein is provided. The method comprises transforming a plant or plant cell with a nucleotide sequence operably linked to one of the regulatory elements of the present disclosure.

11 Claims, 2 Drawing Sheets

Specification includes a Sequence Listing.

Fig. 1

LLDAV FL Regulatory Element  Short ORF   Stem Loop
Putative TATA BOX

ORF 1

1226 bp
1130 bp
904 bp
885 bp
443 bp
113 bp

Fig. 2 cctacgttttttaaggattattatgttgttttaatggtcctcttccaggtatctataccaattggcctgc

LLDAV TR1 (1130bp)

agcacagcaagctacgaagaatgtttcgaatgttctacacaagaaatacaaaggcttcatagaagcaaga acggcggcagatttatactgcaaaaatcatgggttagaacctctcaagttctattctgaagaagctactc ttcaacccaagcagcctaaaagaaaagttccatccggcgaactacccagctcttctctcaaagaagctga

LLDAV TR2 (904bp)   LLDAV TR3 (885bp)

tacaccagatgtaaacattgtcatggaagacttcatgaatgtctacaaggctgcaagagctcattaagat gaacgattcttcatcgaccacttcttcaccaccgagaagaaaaatctaagcttttacaatttctgtgaat gttcagatcctgagatcgtaaaagatgcctatctttgtggattgatcaaaacaatctaccaggtcctaa tctcttggagatttctctccttcctaaagagataagaagaaatgtcaagctattcagacgaaagtgcatt aaagatccaagtaagaaaatttacttgaaattctccagcactattcccagatggggaaaagaaggtgaac aggtttactggccacatcaccatataactatgggtgttcgttccgaagaagaacaataccagccttccag acaaatggaagccacacttgaggttcaagaccttgaagaactagctgttcaaaaaattcaacagttcatc

LLDAV TR4 (443bp)

gaaaagatgtttgaattcagcaaggaagattagacttttgtcaatcttatctggaatagggttttgataa cttcaaaatcttctcaaaccactcagcacaagccatgtggaattgattcttcttttttcaaaagaggttaaa gaatcattatgactttggaccccaccatccactcatatgcaaaagcatagagaaaagtcagtggaatac agctgcctcaactgtagcaaaggcaaaaggccaaagaaagacggacacgtagaagattctgcgacaacgt

LLDAV TR5 (113bp)

cgtcatcatccagctaatgtagttagtggttgattcgtcagcaatgacgtaaaacatttgtatcgatcct cactccttatctataaaaggttgagttattttttcttggaaggacatctcgaaactagcagtcctctcctt tcaaaaaatttatcttttttaagttttttagtcgtcgt

US 11,959,085 B2

REGULATORY ELEMENTS FROM LAMIUM LEAF DISTORTION ASSOCIATED VIRUS (LLDAV)

REFERENCE TO SEQUENCE LISTING SUBMITTED ELECTRONICALLY

A sequence listing having the file name "5970P_Sequence_Listing.TXT" created on Jul. 18, 2014, and having a size of 7.4 kilobytes is filed in computer readable form concurrently with the specification. The sequence listing is part of the specification and is herein incorporated by reference in its entirety.

FIELD

The present disclosure relates to the field of plant molecular biology, more particularly to regulation of gene expression in plants.

BACKGROUND

Expression of heterologous DNA sequences in a plant host is dependent upon the presence of an operably linked regulatory element that is functional within the plant host. Choice of the regulatory element sequence will determine when and where within the organism the heterologous DNA sequence is expressed. Where expression in specific tissues or organs is desired, tissue-preferred regulatory elements may be used. Where gene expression in response to a stimulus is desired, inducible regulatory elements are the regulatory element of choice. In contrast, where continuous expression is desired throughout the cells of a plant, constitutive promoters are utilized. Additional regulatory sequences upstream and/or downstream from the core regulatory element sequence may be included in the expression constructs of transformation vectors to bring about varying levels of expression of heterologous nucleotide sequences in a transgenic plant.

Frequently it is desirable to express a DNA sequence constitutively in a plant. For example, increased resistance of a plant to infection by soil- and air-borne pathogens might be accomplished by genetic manipulation of the plant's genome to comprise a constitutive regulatory element operably linked to a heterologous pathogen-resistance gene such that pathogen-resistance proteins are produced in the desired plant tissue.

Alternatively, it might be desirable to inhibit expression of a native DNA sequence within a plant's tissues to achieve a desired phenotype. In this case, such inhibition might be accomplished with transformation of the plant to comprise a constitutive promoter operably linked to an antisense nucleotide sequence, such that expression of the antisense sequence produces an RNA transcript that interferes with translation of the mRNA of the native DNA sequence.

Genetically altering plants through the use of genetic engineering techniques and thus producing a plant with useful traits requires the availability of a variety of promoters. An accumulation of promoters would enable the investigator to design recombinant DNA molecules that are capable of being expressed at desired levels and cellular locales.

Therefore, a collection of constitutive promoters would allow for a new trait to be expressed at the desired level in the desired tissue. Thus, isolation and characterization of constitutive regulatory elements that can serve as regulatory regions for expression of heterologous nucleotide sequences of interest in a measured constitutive manner are needed for genetic manipulation of plants.

BRIEF SUMMARY

Compositions and methods for regulating expression of a heterologous nucleotide sequence of interest in a plant or plant cell are provided. DNA molecules comprising novel nucleotide sequences for regulatory elements that initiate transcription are provided. In some embodiments the regulatory element has promoter activity initiating transcription in the plant cell. Embodiments of the disclosure comprise the nucleic acid sequence set forth in SEQ ID NO: 1, SEQ ID NO: 2, SEQ ID NO: 3, SEQ ID NO: 4, SEQ ID NO: 5, SEQ ID NO: 6, or a complement thereof, a nucleotide sequence comprising at least 20 contiguous nucleotides of SEQ ID NO: 1, SEQ ID NO: 2, SEQ ID NO: 3, SEQ ID NO: 4, SEQ ID NO: 5, SEQ ID NO: 6, wherein said sequence initiates transcription in a plant cell, and a nucleotide sequence comprising a sequence having at least 85% sequence identity to the sequence set forth in SEQ ID NO: 1, SEQ ID NO: 2, SEQ ID NO: 3, SEQ ID NO: 4, SEQ ID NO: 5, SEQ ID NO: 6, wherein said sequence initiates transcription in the plant cell.

A method for expressing a heterologous nucleotide sequence in a plant or plant cell is provided. The method comprises introducing into a plant or a plant cell an expression cassette comprising a heterologous nucleotide sequence of interest operably linked to one of the regulatory elements of the present disclosure. In this manner, the regulatory element sequences are useful for controlling the expression of the operably linked heterologous nucleotide sequence.

Further provided is a method for expressing a nucleotide sequence of interest in a constitutive manner in a plant. The method comprises introducing into a plant cell an expression cassette comprising a regulatory element of the disclosure operably linked to a heterologous nucleotide sequence of interest.

Expression of the nucleotide sequence of interest may provide for modification of the phenotype of the plant. Such modification includes modulating the production of an endogenous product, as to amount, relative distribution, or the like, or production of an exogenous expression product to provide for a novel function or product in the plant. In specific methods and compositions, the heterologous nucleotide sequence of interest comprises a gene product that confers herbicide resistance, pathogen resistance, insect resistance, and/or altered tolerance to salt, cold, or drought.

Expression cassettes comprising the promoter sequences of the disclosure operably linked to a heterologous nucleotide sequence of interest are provided. Additionally provided are transformed plant cells, plant tissues, seeds, and plants.

BRIEF DESCRIPTION OF THE DRAWINGS

FIG. 1 shows the structure of the Lamium Leaf Distortion Associated Virus (LLDAV) regulatory region and truncations of the regulatory region. The 1226 base pair LLDAV regulatory region (FL) consists of a portion of the long intergenic region (LIR) upstream of a short ORF and stem loop structure. The sequence extends 5' into the 3' end of the last ORF of the LLDAV genome. The regulatory region was truncated (TR) from the 5' end to segments that consisted of 1130 bp, 904 bp, 885 bp, 443 bp, and 113 bp. The position of the putative TATA box is depicted by the arrow.

FIG. 2 shows the nucleic acid sequence of the 1226 base pair full-length LLDAV regulatory element (SEQ ID NO: 1).

The putative TATA box is underlined. Also indicated by inserted arrows are the 5' ends of the truncated LLDAV regulatory elements as represented by the nucleic acid sequence of the 1130 base pair truncated regulatory element LLDAV TR1 (SEQ ID NO: 2), the nucleic acid sequence of the 904 base pair truncated regulatory element LLDAV TR2 (SEQ ID NO: 3), the nucleic acid sequence of the 885 base pair truncated regulatory element LLDAV TR3 (SEQ ID NO: 4), the nucleic acid sequence of the 443 base pair truncated regulatory element LLDAV TR4 (SEQ ID NO: 5), and the nucleic acid sequence of the 113 base pair truncated regulatory element LLDAV TR5 (SEQ ID NO: 6).

DETAILED DESCRIPTION OF THE INVENTION

The disclosure relates to compositions and methods drawn to plant regulatory elements and methods of their use. The compositions comprise nucleotide sequences for the regulatory region of Lamium Leaf Distortion Associated Virus (LLDAV). The compositions further comprise DNA constructs comprising a nucleotide sequence for the regulatory region of LLDAV operably linked to a heterologous nucleotide sequence of interest. In particular, the present disclosure provides for isolated nucleic acid molecules comprising the nucleotide sequence set forth in SEQ ID NO: 1, and fragments, variants, and complements thereof.

The LLDAV regulatory element sequences of the present disclosure include nucleotide constructs that allow initiation of transcription in a plant. In specific embodiments, the LLDAV regulatory element sequence allows initiation of transcription in a constitutive manner. Such constructs of the disclosure comprise regulated transcription initiation regions associated with plant developmental regulation. Thus, the compositions of the present disclosure include DNA constructs comprising a nucleotide sequence of interest operably linked to the LLDAV regulatory element sequence. One source for the LLDAV regulatory region sequence is set forth in SEQ ID NO: 1.

Compositions of the disclosure include the nucleotide sequences for LLDAV regulatory elements and fragments and variants thereof. In specific embodiments, the regulatory element sequences of the disclosure are useful for expressing sequences of interest in a constitutive manner. The nucleotide sequences of the disclosure also find use in the construction of expression vectors for subsequent expression of a heterologous nucleotide sequence in a plant of interest or as probes for the isolation of other LLDAV-like regulatory elements.

Regulatory Elements

A regulatory element is a nucleic acid molecule having gene regulatory activity, i.e. one that has the ability to affect the transcription and/or translation of an operably linked transcribable polynucleotide molecule. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

Regulatory elements such as promoters, leaders, introns, and transcription termination regions are nucleic acid molecules that have gene regulatory activity and play an integral part in the overall expression of genes in living cells. The term "regulatory element" refers to a nucleic acid molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern, i.e. as constitutive and/or by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked nucleic acid molecule into a transcribed RNA molecule. Expression may be characterized by its temporal, spatial, developmental, tissue, environmental, physiological, pathological, cell cycle, and/ or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a nucleic acid molecule that is involved in recognition and binding of RNA polymerase II and other proteins (transacting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules.

In one embodiment, fragments are provided of a promoter sequence disclosed herein. Promoter fragments may exhibit promoter activity, and may be useful alone or in combination with other promoters and promoter fragments, such as in constructing chimeric promoters. In specific embodiments, fragments of a promoter are provided comprising at least about 50, 95, 150, 250, 500, or about 750 contiguous nucleotides of a polynucleotide molecule having promoter activity disclosed herein. Such fragments may exhibit at least about 85 percent, about 90 percent, about 95 percent, about 98 percent, or about 99 percent, or greater, identity with a reference sequence when optimally aligned to the reference sequence.

A promoter or promoter fragment may also be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements may be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present disclosure.

As used herein, the term "5' untranslated flanking region" refers to a DNA molecule isolated from the untranslated 5' region (5' UTR) of a genomic copy of a gene and defined generally as a nucleotide segment between the transcription start site (TSS) and the protein coding sequence start site. These sequences, or leaders, may be synthetically produced or manipulated DNA elements. A leader may be used as a 5' regulatory element for modulating expression of an operably linked transcribable polynucleotide molecule. Leader molecules may be used with a heterologous promoter or with their native promoter. Promoter molecules of the present disclosure may thus be operably linked to their native leader or may be operably linked to a heterologous leader.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present disclosure.

It is to be understood that nucleotide sequences, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present disclosure a post-transcriptional regulatory element may include elements that are active following transcription initiation, for example translational and transcriptional enhancers, translational and transcriptional repressors, and mRNA stability determinants.

The regulatory elements, or variants or fragments thereof, of the present disclosure may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element and modulating post-transcriptional events. For example, one or more regulatory elements, or fragments thereof, of the present disclosure may be operatively associated with constitutive, inducible, or tissue specific promoters or fragment thereof, to modulate the activity of such promoters within desired tissues in plant cells.

The disclosure encompasses isolated or recombinant nucleic acid compositions. An "isolated" or "recombinant" nucleic acid molecule (or DNA) is used herein to refer to a nucleic acid sequence (or DNA) that is no longer in its natural environment, for example in an in vitro or in a heterologous recombinant bacterial or plant host cell. An isolated or recombinant nucleic acid molecule, or biologically active portion thereof, is substantially free of other cellular material or culture medium when produced by recombinant techniques, or substantially free of chemical precursors or other chemicals when chemically synthesized. An isolated or recombinant nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. The LLDAV regulatory element sequences of the disclosure may be isolated from the 5' untranslated region flanking their respective transcription initiation sites.

Fragments and variants of the disclosed promoter nucleotide sequences are also encompassed by the present disclosure. In particular, fragments and variants of the LLDAV regulatory element sequence of SEQ ID NO: 1, SEQ ID NO: 2 or SEQ ID NO: 3, SEQ ID NO: 4, SEQ ID NO: 5, and/or SEQ ID NO: 6 may be used in the DNA constructs of the disclosure. As used herein, the term "fragment" refers to a portion of the nucleic acid sequence. Fragments of an LLDAV regulatory element sequence may retain the biological activity of initiating transcription, more particularly driving transcription in a constitutive manner. Alternatively, fragments of a nucleotide sequence which are useful as hybridization probes may not necessarily retain biological activity. Fragments of a nucleotide sequence for the LLDAV regulatory region may range from at least about 20 nucleotides, about 50 nucleotides, about 100 nucleotides, and up to the full-length nucleotide sequence of the disclosure for the promoter region of the gene.

A biologically active portion of an LLDAV regulatory element can be prepared by isolating a portion of the LLDAV regulatory element sequence of the disclosure, and assessing the promoter activity of the portion. Nucleic acid molecules that are fragments of a LLDAV regulatory element nucleotide sequence comprise at least about 16, 50, 75, 100, 150, 200, 250, 300, 350, 400, 450, 500, 550, 600, 650, 700, 800, 900 or 1000 nucleotides, or up to the number of nucleotides present in a full-length LLDAV regulatory element sequence disclosed herein (for example, 1226 nucleotides for SEQ ID NO: 1).

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" or "genomic" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein. A biologically active variant of a nucleotide sequence of the disclosure may differ from that sequence by as few as 1-15 nucleic acid residues, as few as 1-10, as few as 6-10, as few as 5, as few as 4, 3, 2, or even 1 nucleic acid residue.

In some embodiments the nucleic acid molecule encoding the regulatory region is a "non-genomic nucleic acid sequence". As used herein a "non-genomic nucleic acid sequence" refers to a nucleic acid molecule that has one or more changes in the nucleic acid sequence compared to the native or genomic nucleic acid sequence.

Variant nucleotide sequences also encompass sequences derived from a mutagenic and recombinogenic procedure such as DNA shuffling. With such a procedure, LLDAV regulatory element nucleotide sequences can be manipulated to create new LLDAV regulatory elements. In this manner, libraries of recombinant polynucleotides are generated from a population of related sequence polynucleotides comprising sequence regions that have substantial sequence identity and may be homologously recombined in vitro or in vivo. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

The nucleotide sequences of the disclosure can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire LLDAV regulatory element sequence set forth herein or to fragments thereof are encompassed by the present disclosure.

In a PCR approach, oligonucleotide primers can be designed for use in PCR reactions to amplify corresponding DNA sequences from genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, New York), hereinafter Sambrook. See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments from a chosen organism. The hybridization probes may be labeled with a detectable group such as P-32 or any other detectable marker. Thus, for example, probes for hybridization can be made by labeling synthetic oligonucleotides based on the LLDAV regulatory element sequence of the disclosure. Methods for preparation of probes for hybridization and for construction of genomic libraries are generally known in the art and are disclosed in Sambrook.

For example, the entire LLDAV regulatory element sequence disclosed herein, or one or more portions thereof, may be used as a probe capable of specifically hybridizing to corresponding LLDAV regulatory element sequences and messenger RNAs. To achieve specific hybridization under a variety of conditions, such probes include sequences that are unique among LLDAV regulatory element sequences and are at least about 10 nucleotides in length or at least about 20 nucleotides in length. Such probes may be used to amplify corresponding LLDAV regulatory element sequences from a chosen plant by PCR. This technique may be used to isolate additional coding sequences from a desired organism, or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The terms "stringent conditions" or "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions may be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the Tm (thermal melting point) can be approximated from the equation of Meinkoth and Wahl (1984) Anal. Biochem. 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm. Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See also Sambrook.

Thus, isolated sequences that have constitutive promoter activity and which hybridize under stringent conditions to the LLDAV regulatory element sequences disclosed herein, or to fragments thereof, are encompassed by the present disclosure.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, California, USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the website for the National Center for Biotechnology Information. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. An "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80%, at least 90%, and at least 95%, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the Tm for the specific sequence at a defined ionic strength and pH. However, stringent conditions encompass temperatures in the range of about 1° C. to about 20° C. lower than the Tm, depending upon the desired degree of stringency as otherwise qualified herein.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the disclosure, provided that these parts comprise the introduced polynucleotides.

The present disclosure may be used for transformation of any plant species, including, but not limited to, monocots and dicots. Examples of plant species include corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), Eupatoriums (*Eupatorium hybrida*), carnation (*Dianthus caryophyllus*), poinsettia (*Euphorbia pulcherrima*), and chrysanthemum.

Conifers that may be employed in practicing the present disclosure include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*). In specific embodiments, plants of the present disclosure are crop plants (for example, corn, alfalfa, sunflower, *Brassica*, soybean, cotton, safflower, peanut, *sorghum*, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mung bean, lima bean, fava bean, lentils, chickpea, etc.

As used herein, the term "transcribable polynucleotide molecule" refers to any DNA molecule capable of being transcribed into a RNA molecule, including, but not limited to, those having protein coding sequences and those having sequences useful for gene suppression. A "transgene" refers to a transcribable polynucleotide molecule heterologous to a host cell and/or a transcribable polynucleotide molecule artificially incorporated into a host cell's genome.

A regulatory element of the present invention may be operably linked to a transcribable polynucleotide molecule that is heterologous with respect to the regulatory molecule. As used herein, the term "heterologous" refers to the combination of two or more polynucleotide molecules when such a combination would not normally be found in nature. For example, the two molecules may be derived from different species and/or the two molecules may be derived from different genes, e.g. different genes from the same species or the same genes from different species. A regulatory element is thus heterologous with respect to an operably linked transcribable polynucleotide molecule if such a combination is not normally found in nature, i.e. that transcribable polynucleotide molecule is not naturally occurring operably linked in combination with that regulatory element molecule.

The transcribable polynucleotide molecule may generally be any DNA molecule for which expression of an RNA transcript is desired. Such expression of an RNA transcript may result in translation of the resulting mRNA molecule and thus protein expression. Alternatively, a transcribable polynucleotide molecule may be designed to ultimately cause decreased expression of a specific gene or protein. This may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complementary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NO: 1-6, operably linked to a transcribable polynucleotide molecule so as to modulate transcription of the transcribable polynucleotide molecule at a desired level or in a desired pattern upon introduction of said construct into a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule or other similar inhibitory RNA molecule in order to inhibit expression of a specific RNA molecule of interest in a target host cell.

Transcribable polynucleotide molecules expressed by the LLDAV regulatory elements of the disclosure may be used for varying the phenotype of a plant. Various changes in phenotype are of interest including modifying expression of a gene, altering a plant's pathogen or insect defense mechanism, increasing the plants tolerance to herbicides in a plant, altering root development to respond to environmental stress, modulating the plant's response to salt, temperature (hot and cold), drought, and the like. These results can be achieved by the expression of a heterologous nucleotide sequence of interest comprising an appropriate gene product. In specific embodiments, the heterologous nucleotide sequence of interest is an endogenous plant sequence whose expression level is increased in the plant or plant part. Alternatively, the results can be achieved by providing for a reduction of expression of one or more endogenous gene products, particularly enzymes, transporters, or cofactors, or by affecting nutrient uptake in the plant. These changes result in a change in phenotype of the transformed plant.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type provides a desirable characteristic associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment, a regulatory element of the present disclosure is incorporated into a construct such that the regulatory is operably linked to a transcribable polynucleotide molecule that is a gene of agronomic interest. The expression of the gene of agronomic interest is desirable in order to confer an agronomically beneficial trait. A beneficial agronomic trait may be, for example, but not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production.

Insect resistance genes may encode resistance to pests that damage and cause yield drag such as rootworm, cutworm, European corn borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48:109); and the like.

Genes encoding disease resistance traits include detoxification genes, such as those which detoxify fumonisin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), glyphosate (e.g., the EPSPS gene and the GAT gene; see, for example, U.S. Publication No. 20040082770 and WO 03/092360) or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,714,188 and 7,462,481.

Genes of agronomic interest with regulatory approval are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications isaaa.org/gmapprovaldatabase/default.asp, which can be accessed using the www prefix).

Exogenous products include plant enzymes and products as well as those from other sources including prokaryotes and other eukaryotes. Such products include enzymes, cofactors, hormones, and the like.

Examples of other applicable genes and their associated phenotype include the gene which encodes viral coat protein and/or RNA, or other viral or plant genes that confer viral resistance; genes that confer fungal resistance; genes that promote yield improvement; and genes that provide for resistance to stress, such as cold, dehydration resulting from drought, heat and salinity, toxic metal or trace elements, or the like.

As noted, the heterologous nucleotide sequence operably linked to the LLDAV regulatory element disclosed herein may be an antisense sequence for a targeted gene. Thus the promoter sequences disclosed herein may be operably linked to antisense DNA sequences to reduce or inhibit expression of a native protein in the plant root.

"RNAi" refers to a series of related techniques to reduce the expression of genes (See for example U.S. Pat. No. 6,506,559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The LLDAV regulatory element of the embodiments may be used to drive expression of constructs that will result in RNA interference including microRNAs and siRNAs.

The regulatory element sequences of the present disclosure, or variants or fragments thereof, when operably linked to a heterologous nucleotide sequence of interest may drive constitutive expression of the heterologous nucleotide sequence in the plant expressing this construct. A "heterologous nucleotide sequence" is a sequence that is not naturally occurring with the regulatory element sequence of the disclosure. While this nucleotide sequence is heterologous to the regulatory element sequence, it may be homologous, or native, or heterologous, or foreign, to the plant host.

The isolated regulatory element sequences of the present disclosure may be modified to provide for a range of expression levels of the heterologous nucleotide sequence. Thus, less than the entire regulatory element region may be utilized and the ability to drive expression of the nucleotide sequence of interest retained. It is recognized that expression levels of the mRNA may be altered in different ways with deletions of portions of the regulatory element sequences. The mRNA expression levels may be decreased, or alternatively, expression may be increased as a result of regulatory element deletions if, for example, there is a negative regulatory element (for a repressor) that is removed during the truncation process. Generally, at least about 20 nucleotides of an isolated regulatory element sequence will be used to drive expression of a nucleotide sequence.

It is recognized that to increase transcription levels, enhancers may be utilized in combination with the regulatory element regions of the disclosure. Enhancers are nucleotide sequences that act to increase the expression of a regulatory element region. Enhancers are known in the art and include the SV40 enhancer region, the 35S enhancer element, and the like. Some enhancers are also known to alter normal regulatory element expression patterns, for example, by causing a regulatory element to drive expression constitutively when without the enhancer, the same regulatory element drives expression only in one specific tissue or a few specific tissues.

Modifications of the isolated regulatory element sequences of the present disclosure can provide for a range of expression of the heterologous nucleotide sequence. Thus, they may be modified to be weak promoters or strong promoters. Generally, a "weak promoter" means a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

It is recognized that the LLDAV regulatory elements of the disclosure may be used to increase or decrease expression, thereby resulting in a change in phenotype of the transformed plant. This phenotypic change could further affect an increase or decrease in levels of metal ions in tissues of the transformed plant.

The nucleotide sequences disclosed in the present disclosure, as well as variants and fragments thereof, are useful in the genetic manipulation of a plant. The LLDAV regulatory element sequence is useful in this aspect when operably linked with a heterologous nucleotide sequence whose expression is to be controlled to achieve a desired phenotypic response. The term "operably linked" means that the transcription or translation of the heterologous nucleotide sequence is under the influence of the regulatory element sequence. In this manner, the nucleotide sequences for the regulatory elements of the disclosure may be provided in expression cassettes along with heterologous nucleotide sequences of interest for expression in the plant of interest, more particularly for expression in the root of the plant.

The regulatory sequences of the embodiments are provided in DNA constructs for expression in the organism of interest. An "expression cassette" as used herein means a DNA construct comprising a regulatory sequence of the embodiments operably linked to a heterologous polynucleotide encoding a polypeptide of interest. Such expression cassettes will comprise a transcriptional initiation region comprising one of the regulatory element nucleotide sequences of the present disclosure, or variants or fragments thereof, operably linked to the heterologous nucleotide sequence. Such an expression cassette can be provided with a plurality of restriction sites for insertion of the nucleotide sequence to be under the transcriptional regulation of the regulatory regions. The expression cassette may additionally contain selectable marker genes as well as 3' termination regions.

The expression cassette can include, in the 5'-3' direction of transcription, a transcriptional initiation region (i.e., a promoter, or variant or fragment thereof, of the disclosure), a translational initiation region, a heterologous nucleotide sequence of interest, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, may be native with the operably linked DNA sequence of interest, may be native with the plant host, or may be derived from another source (i.e., foreign or heterologous to the promoter, the DNA sequence being expressed, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

The expression cassette comprising the sequences of the present disclosure may also contain at least one additional nucleotide sequence for a gene to be cotransformed into the organism. Alternatively, the additional sequence(s) can be provided on another expression cassette.

Where appropriate, the nucleotide sequences whose expression is to be under the control of the constitutive promoter sequence of the present disclosure and any additional nucleotide sequence(s) may be optimized for increased expression in the transformed plant. That is, these nucleotide sequences can be synthesized using plant preferred codons for improved expression. See, for example, Campbell and Gowri (1990) Plant Physiol. 92:1-11 for a discussion of host-preferred codon usage. Methods are available in the art for synthesizing plant-preferred genes. See, for example, U.S. Pat. Nos. 5,380,831, 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy Stein et al. (1989) Proc. Nat. Acad. Sci. USA 86:6126 6130); potyvirus leaders, for example, TEV leader (Tobacco Etch Virus) (Allison et al. (1986) Virology 154:9 20); MDMV leader (Maize Dwarf Mosaic Virus); human immunoglobulin heavy chain binding protein (BiP) (Macejak et al. (1991) Nature 353:90 94); untranslated leader from the coat protein mRNA of alfalfa mosaic virus (AMV RNA 4) (Jobling et al. (1987) Nature 325:622 625); tobacco mosaic virus leader (TMV) (Gallie et al. (1989) Molecular Biology of RNA, pages 237 256); and maize chlorotic mottle virus leader (MCMV) (Lommel et al. (1991) Virology 81:382 385). See also Della Cioppa et al. (1987) Plant Physiology 84:965 968. Methods known to enhance mRNA stability can also be utilized, for example, introns, such as the maize Ubiquitin intron (Christensen and Quail (1996) Transgenic Res. 5:213-218; Christensen et al. (1992) Plant Molecular Biology 18:675-689) or the maize Adhl intron (Kyozuka et al. (1991) Mol. Gen. Genet. 228:40-48; Kyozuka et al. (1990) Maydica 35:353-357), and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may be included in the expression cassettes. Examples of suitable reporter genes known in the art can be found in, for example, Jefferson et al. (1991) in Plant Molecular Biology Manual, ed. Gelvin et al. (Kluwer Academic Publishers), pp. 1-33; DeWet et al. (1987) Mol. Cell. Biol. 7:725-737; Goff et al. (1990) EMBO J. 9:2517-2522; Kain et al. (1995) BioTechniques 19:650-655; and Chiu et al. (1996) Current Biology 6:325-330.

Selectable marker genes for selection of transformed cells or tissues may include genes that confer antibiotic resistance or resistance to herbicides. Examples of suitable selectable marker genes include, but are not limited to, genes encoding resistance to chloramphenicol (Herrera Estrella et al. (1983) EMBO J. 2:987-992); methotrexate (Herrera Estrella et al. (1983) Nature 303:209-213; Meijer et al. (1991) Plant Mol. Biol. 16:807-820); hygromycin (Waldron et al. (1985) Plant Mol. Biol. 5:103-108; and Zhijian et al. (1995) Plant Science 108:219-227); streptomycin (Jones et al. (1987) Mol. Gen. Genet. 210:86-91); spectinomycin (Bretagne-Sagnard et al. (1996) Transgenic Res. 5:131-137); bleomycin (Hille et al. (1990) Plant Mol. Biol. 7:171-176); sulfonamide (Guerineau et al. (1990) Plant Mol. Biol. 15:127-136); bromoxynil (Stalker et al. (1988) Science 242:419-423); glyphosate (Shaw et al. (1986) Science 233:478-481; and U.S. application Ser. Nos. 10/004,357; and 10/427,692); phosphinothricin (DeBlock et al. (1987) EMBO J. 6:2513-2518).

Other genes that could serve utility in the recovery of transgenic events but might not be required in the final product would include, but are not limited to, examples such as GUS (beta-glucuronidase; Jefferson (1987) Plant Mol. Biol. Rep. 5:387), GFP (green fluorescence protein; Chalfie et al. (1994) Science 263:802), luciferase (Riggs et al. (1987) Nucleic Acids Res. 15(19):8115 and Luehrsen et al. (1992) Methods Enzymol. 216:397-414) and the maize genes encoding for anthocyanin production (Ludwig et al. (1990) Science 247:449).

The expression cassette comprising the LLDAV regulatory elements of the present disclosure operably linked to a nucleotide sequence of interest may be used to transform any plant. In this manner, genetically modified plants, plant cells, plant tissue, seed, root, and the like can be obtained.

The methods of the disclosure involve introducing a polypeptide or polynucleotide into a plant. "Introducing" is intended to mean presenting to the plant the polynucleotide or polypeptide in such a manner that the sequence gains access to the interior of a cell of the plant. The methods of the disclosure do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320 334), electroporation (Riggs et al. (1986) Proc. Natl. Acad. Sci. USA 83:5602 5606), Agrobacterium-mediated transformation (Townsend et al., U.S. Pat. No. 5,563,055 and Zhao et al., U.S. Pat. No.

5,981,840), direct gene transfer (Paszkowski et al. (1984) EMBO J. 3:2717 2722), and ballistic particle acceleration (see, for example, U.S. Pat. Nos. 4,945,050; 5,879,918; 5,886,244; 5,932,782; Tomes et al. (1995) in Plant Cell, Tissue, and Organ Culture: Fundamental Methods, ed. Gamborg and Phillips (Springer-Verlag, Berlin); McCabe et al. (1988) Biotechnology 6:923 926); and Lec1 transformation (WO 00/28058). Also see Weissinger et al. (1988) Ann. Rev. Genet. 22:421 477; Sanford et al. (1987) Particulate Science and Technology 5:27 37 (onion); Christou et al. (1988) Plant Physiol. 87:671 674 (soybean); McCabe et al. (1988) Bio/Technology 6:923 926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736 740 (rice); Klein et al. (1988) Proc. Natl. Acad. Sci. USA 85:4305 4309 (maize); Klein et al. (1988) Biotechnology 6:559 563 (maize); U.S. Pat. Nos. 5,240,855; 5,322,783 and 5,324,646; Klein et al. (1988) Plant Physiol. 91:440 444 (maize); Fromm et al. (1990) Biotechnology 8:833 839 (maize); Hooykaas-Van Slogteren et al. (1984) Nature (London) 311:763-764; U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference.

In specific embodiments, the DNA constructs comprising the regulatory element sequences of the disclosure can be provided to a plant using a variety of transient transformation methods. Such transient transformation methods include, but are not limited to, viral vector systems and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma-Aldrich™ #P3143).

In other embodiments, the polynucleotide of the disclosure may be introduced into plants by contacting plants with a virus or viral nucleic acids. Generally, such methods involve incorporating a nucleotide construct of the disclosure within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) Molecular Biotechnology 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the disclosure can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct of the disclosure, for example, an expression cassette of the disclosure, stably incorporated into its genome.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications, patents and patent applications mentioned in the specification are indicative of the level of those skilled in the art to which this disclosure pertains. All publications, patents and patent applications are herein incorporated by reference to the same extent as if each individual publication, patent or patent application was specifically and individually indicated to be incorporated by reference.

The above description of various illustrated embodiments of the disclosure is not intended to be exhaustive or to limit the scope to the precise form disclosed. While specific embodiments of examples are described herein for illustrative purposes, various equivalent modifications are possible within the scope of the disclosure, as those skilled in the relevant art will recognize. The teachings provided herein can be applied to other purposed, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

Efforts have been made to ensure accuracy with respect to the numbers used (e.g. amounts, temperature, concentrations, etc.), but some experimental errors and deviations should be allowed for. Unless otherwise indicated, parts are parts by weight; molecular weight is average molecular weight; temperature is in degrees centigrade; and pressure is at or near atmospheric.

The following examples are offered by way of illustration and not by way of limitation.

EXPERIMENTAL

Example 1: Lamium Leaf Distortion Associated Virus Regulatory Element Sequences

The regulatory element of SEQ ID NO: 1 was obtained through a search of GenBank Genomes for viral genomes that had been sequenced and belonged to the Caulimoviridae virus family. The search was initiated based on the well-known Cauliflower Mosaic Virus 35S (CaMV35S) promoter. It drives constitutive expression of heterologous genes in most tissues of most plants. Other regulatory elements from this virus family, such as the Figwort Mosaic Virus 34S promoter also direct constitutive-like expression in plants. Therefore, additional regulatory elements derived from the Caulimoviridae virus family also may drive constitutive expression in plants. The region of the genome found in what is called the Long Intergenic Region (LIR) generally contains the regulatory sequences necessary for promoter function in plants.

The Lamium Leaf Distortion Associated Virus (LLDAV) genome has an LIR, so this region was targeted for functional analysis of regulatory elements. One full-length sequence was selected to be tested in plants. The sequence consists of 1226 bp (set forth in SEQ ID NO: 1) and has a putative TATA box starting approximately 95 bp upstream of the 3' end of the sequence. The entire 1226 bp sequence is referred to as the LLDAV full-length regulatory element or LLDAV FL. Deleting segments of the 5' end of the full-length regulatory element may alter the expression pattern and provide insight into important sequence markers in the regulatory region. Second, third, fourth, fifth and sixth sequences are a truncated version of the full-length regulatory element (See FIG. 2; SEQ ID NO: 1). LLDAV TR1, LLDAV TR2, LLDAV TR3, LLDAV TR4, and LLDAV TR5 regulatory elements respectively consist of 1130 bp, 904 bp, 885 bp, 443 bp, and 113 bp and contain the 3' end of the full-length promoter (SEQ ID NO: 2-6).

Example 2: Expression and Deletion Analysis of the LLDAV Regulatory Element

LLDAV FL was operably linked to the first intron of the maize alcohol dehydrogenase gene 1 (ADH1 intron1) and the β-glucuronidase (GUS) gene, in an expression vector, to test whether the synthesized DNA fragment would direct expression (SEQ ID NO: 1). ADH1 intron1 was included for the purpose of increased expression as it has been shown that in cereal plant cells the expression of transgenes is enhanced by the presence of some 5' proximal introns (See Callis et al. (1987) *Genes and Development* 1: 1183-1200; Kyozuka et al. (1990) *Maydica* 35:353-357).

The Ubi-1 promoter and intron from *Zea mays* were operably linked to the GUS gene so that it could be used to compare the expression pattern and expression levels of the LLDAV regulatory elements. The Ubi-1 promoter is a strong constitutive promoter in most tissues of *Zea mays*.

Regulatory elements are a collection of sequence motifs that work together to bind transcription factors that result in the spatial, temporal, and quantitative expression characteristics of a promoter. Understanding the architecture and the positioning of these motifs enhances knowledge pertaining to the regulatory element. Segmental deletion analysis is an important tool that can be used to begin to identify regions of a regulatory element that contain functionally important motifs. The removal of segments from the 5' end may change the spatial, temporal, and/or quantitative expression patterns directed by the regulatory element. The regions that result in a change may then be studied more closely to evaluate the sequences and their interaction with cis and trans factors. The truncations may also identify a minimal functional sequence.

The restriction endonuclease recognition sites, SfuI, AccI, SacI, EcoRI and ClaI were used to remove five sequence regions of LLDAV FL ranging in size from ~96 to 1113 bp. LLDAV TR1, LLDAV TR2, LLDAV TR3, LLDAV TR4, LLDAV TR5 were operably linked to ADH1 intron1 and the GUS gene in an expression vector to test the expression potential of the synthesized DNA fragments (SEQ ID NO: 2-6).

Stable transformed maize plants were created using *Agrobacterium* protocols (detailed in Example 3) to allow for the characterization of promoter activity, including spatial and quantitative expression directed by the different regulatory elements. Plants grown to V5/6 stage under greenhouse conditions were sampled for leaf and root material to evaluate expression pattern changes via histochemical GUS staining analysis and quantitative fluorometric assays. Maize vegetative growth stages are determined by the number of collared leaves on the plant. Therefore, a plant at V5 stage has 5 fully collared leaves. Tissues were also collected when the plants reached the reproductive growth stages of R1-R2. R1 is noted by the emergence of silks outside the husk and R2 is when the silks start to dry out. Results showed that LLDAV FL drove expression in most tissues of maize similar to or slightly better than the Ubi-1 promoter (Table 1). The exception was pollen, where LLDAV FL expression was much lower than Ubi-1. The 5' truncated promoters (LLDAV TR1-4) performed similarly to LLDAV FL with the exception of LLDAV TR5 which did not function in any of the tissues tested.

TABLE 1

Plant Expression Results for the LLDAV Promoter (with ADH1 intron1 and GUS)

| | V5-V6 | | | R1-R2 | | | |
|---|---|---|---|---|---|---|---|
| | Leaf | Root | Stalk | Tassel | Husk | Silk | Pollen |
| LLDAV FL | 4 | 3 | 3 | 3 | 5 | 2 | <0.1 |
| LLDAV TR1 | 4 | 3 | 3 | 3 | 5 | 2 | <0.1 |
| LLDAV TR2 | 4 | 3 | 3 | 3 | 5 | 2 | <0.1 |
| LLDAV TR3 | 4 | 3.5 | 3.25 | 3 | 5 | 2 | <0.1 |
| LLDAV TR4 | 4 | 3 | 3 | 3 | 5 | 2 | <0.1 |
| LLDAV TR5 | 0 | 0 | 0 | 0 | 0 | 0 | 0 |
| Ubi-1 | 3 | 3 | 3 | 3 | 5 | 2 | 3 |
| untransformed (negative control) | 0 | 0 | 0 | 0 | 0 | 0 | 0 |

Data expressed on a 0-6 scale with the maize Ubi-1 promoter directed expression as a comparator.

The LLDAV FL (SEQ ID NO: 1) regulatory element was operably linked to ADH1 intron1 and an insecticidal gene (abbreviated IG2) to test expression. The Ubi-1 promoter and intron driving the expression of the IG2 insecticidal gene was used for comparison in the analysis. Stable transformed maize plants were created using *Agrobacterium* protocols (detailed in Example 3) and allowed to grow to V5/6 stage when leaves were sampled. The plants were then allowed to grow to R1-R2 stage when stalk and pollen samples were taken. Kernels were sampled when they reached maturity.

Results from enzyme-linked immunosorbent assays (ELISA) against IG2 showed the LLDAV FL regulatory element (SEQ ID NO: 1) directed expression in leaf, stalk, and kernel tissues (Table 2). Expression levels were comparable to the Ubi-1 promoter and its intron in leaf and stalk tissues. In kernels, LLDAV FL (SEQ ID NO: 1) directed expression was lower than Ubi-1 and in pollen expression was very low.

The expression data were supported by results from insect consumption assays. Feeding insects dissected plant tissues provides a rapid assessment of protein expression, as sufficient levels are needed to protect the tissue from the insects. Insufficient expression will result in feeding damage. Both LLDAV FL (SEQ ID NO: 1) and Ubi-1 plants demonstrated levels of expression that protected leaf and silk tissue against insect damage. Tissues from negative control plants that did not have the IG2 gene were consumed.

TABLE 2

Plant Expression Results for the LLDAV Regulatory Element (with ADH1 intron1 and LLDAV:IG2) Data expressed on a 0-6 scale with the maize Ubi-1 promoter representing a median value.

|  | V5-V6 | | R1-R2 | Maturity |
|---|---|---|---|---|
|  | Leaf | Stalk | Pollen | Kernels |
| LLDAV FL | 2 | 3 | <0.1 | <0.75 |
| Ubi-1 | 2 | 3 | 3 | 2 |
| untransformed (negative control) | 0 | 0 | 0 | 0 |

Data expressed on a 0-6 scale with the maize Ubi-1 promoter representing a median value.

Example 3: *Agrobacterium*-Mediated Transformation of Maize and Regeneration of Transgenic Plants For *Agrobacterium*-mediated transformation of maize with a regulatory element sequence of the disclosure, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium* under conditions whereby the bacteria were capable of transferring the regulatory element sequence of the disclosure to at least one cell of at least one of the immature embryos (step 1: the infection step). The embryos were co-cultured with the *Agrobacterium* suspension for a period of time then co-cultured on solid medium (step 2: the co-cultivation step). An optional "resting" step was performed following co-cultivation. In this resting step, the embryos were incubated in the presence of at least one antibiotic known to inhibit the growth of *Agrobacterium* without the addition of a selective agent for plant transformants (step 3: resting step). Next, the embryos were transferred and cultured on medium containing a selective agent to recover growing, transformed calli (step 4: the selection step). Plantlets were regenerated from calli (step 5: the regeneration step) prior to transfer to the greenhouse.

Example 4: Expression Analysis of the LLDAV Regulatory Element in Canola

The LLDAV promoter was tested in canola using the GUS gene as a reporter. Biolistic bombardment transient assays were used to provide an initial assessment of performance. The number of GUS staining foci and the intensity of staining was compared to the *Arabidopsis* ubiqutin-10 promoter (AtUBQ10), a strong promoter in canola tissues. Performance of the LLDAV promoter was similar to the AtUBQ10 promoter in regard to the intensity of GUS staining. However, a slight reduction in the number of staining foci was observed (Table 3).

Transgenic canola plants were regenerated with both the LLDAV:GUS and AtUBQ10:GUS vectors. Histochemical staining of LLDAV:GUS events showed high levels of expression in leaves and floral organs (Table 3). LLDAV directed expression was also observed in pollen and siliques. When compared against histochemically stained tissue from AtUBQ10:GUS plants, LLDAV was comparable in leaves and floral organs. In pollen, LLDAV directed expression was weaker than AtUBQ10 with about 10-15% of the pollen grains staining. Almost all of the AtUBQ10 pollen grains stained darkly.

TABLE 3

Expression Results for the LLDAV Promoter in Canola

|  | Transient assay | Leaf | Floral organs | Pollen |
|---|---|---|---|---|
| LLDAV FL | 2 | 3 | 3 | 1 |
| AtUBQ10 | 3 | 3 | 3 | 3 |

Data expressed on a 0-3 scale with three indicating strong expression.

What is claimed is:

1. A recombinant polynucleotide comprising one or more enhancer sequences operably linked to a regulatory element having promoter activity operably linked to a heterologous polynucleotide, wherein the regulatory element comprises a polynucleotide having the nucleic acid sequence of SEQ ID NO: 1, SEQ ID NO: 2, SEQ ID NO: 3, SEQ ID NO: 4, or SEQ ID NO: 5, wherein the recombinant polynucleotide further comprises one or more intron sequences operably linked to the regulatory element, and wherein the enhancer sequence is derived from a virus and the intron sequence is derived from *Zea mays*.

2. A DNA construct comprising
   (a) one or more enhancer sequences operably linked to a regulatory element polynucleotide having a nucleic acid sequence selected from the group consisting of SEQ ID NO: 1, SEQ ID NO: 2, SEQ ID NO: 3, SEQ ID NO: 4, and SEQ ID NO: 5 operably linked to one or more intron sequences, and
   (b) a heterologous transcribable polynucleotide molecule operably linked to the regulatory element polynucleotide, wherein the regulatory element polynucleotide has promoter activity.

3. The DNA construct of claim 2, wherein the heterologous transcribable polynucleotide molecule is a gene of agronomic interest.

4. The DNA construct of claim 3, wherein the heterologous transcribable polynucleotide molecule is a gene capable of providing herbicide resistance in plants.

5. The DNA construct of claim 3, wherein the heterologous transcribable polynucleotide molecule is a gene capable of providing plant pest control in plants.

6. A cell stably transformed with the recombinant polynucleotide of claim 1.

7. A transgenic plant or plant cell stably transformed with the DNA construct of claim 2.

8. The transgenic plant or plant cell of claim 7, wherein the transgenic plant or plant cell is a dicotyledon.

9. The transgenic plant or plant cell of claim 7, wherein the transgenic plant or plant cell is a monocotyledon.

10. A seed of the transgenic plant of claim 7, wherein the seed comprises the DNA construct.

11. A method for expressing a heterologous nucleotide sequence in a maize plant or plant cell comprising introducing into a maize plant or plant cell a DNA construct comprising:
   (a) one or more enhancer sequences operably linked to a regulatory element polynucleotide having a nucleic acid sequence selected from the group consisting of SEQ ID NO: 1, SEQ ID NO: 2, SEQ ID NO: 3, SEQ ID NO: 4, and SEQ ID NO: 5 operably linked to one or more intron sequences, and
   (b) a heterologous transcribable polynucleotide molecule operably linked to the regulatory element polynucleotide, wherein the regulatory element polynucleotide has promoter activity; and
   (c) wherein the heterologous transcribable nucleotide sequence is expressed in said maize plant or plant cell.

\* \* \* \* \*

SEQUENCE LISTING

```
<160> NUMBER OF SEQ ID NOS: 6

<210> SEQ ID NO 1
<211> LENGTH: 1226
<212> TYPE: DNA
<213> ORGANISM: Lamium Leaf Distortion Associated Virus
<220> FEATURE:
<221> NAME/KEY: promoter
<222> LOCATION: (1)..(1226)
<223> OTHER INFORMATION: LLDAV FL Promoter Sequence

<400> SEQUENCE: 1
cctacgtttt taaggattat tatgttgttt ttaatggtcc tcttccaggt atctatacca      60
attggcctgc agcacagcaa gctacgaaga atgtttcgaa tgttctacac aagaaataca     120
```

```
aaggcttcat agaagcaaga acggcggcag atttatactg caaaaatcat gggttagaac    180
ctctcaagtt ctattctgaa gaagctactc ttcaacccaa gcagcctaaa agaaaagttc    240
catccggcga actacccagc tcttctctca agaagctga tacaccagat gtaaacattg     300
tcatggaaga cttcatgaat gtctacaagg ctgcaagagc tcattaagat gaacgattct    360
tcatcgacca cttcttcacc accgagaaga aaatctaag cttttacaat ttctgtgaat     420
gttcagatcc tgagatcgta aaagatgcct atctttgtgg attgatcaaa acaatctacc    480
caggtcctaa tctcttggag atttctctcc ttcctaaaga gataagaaga aatgtcaagc    540
tattcagacg aaagtgcatt aaagatccaa gtaagaaaat ttacttgaaa ttctccagca    600
ctattcccag atggggaaaa gaaggtgaac aggtttactg ccacatcac catataacta    660 tgggtgttcg ttccgaagaa gaacaatacc agccttccag acaaatggaa gcccacacttg   720 aggttcaaga ccttgaagaa ctagctgttc aaaaaattca acagttcatc gaaaagatgt    780
ttgaattcag caaggaagat tagacttttg tcaatcttat ctggaatagg gttttgataa    840
cttcaaaatc tttcaaacca ctcagcacaa gccatgtgga attgattctt cttttcaaa    900 agaggtaaaa gaatcattat gactttggac cccaccatcc actcatatgc aaaagcatag    960
agaaaaagtc agtggaatac agctgcctca actgtagcaa aggcaaaagg ccaaagaaag   1020
acggacacgt agaagattct gcgacaacgt cgtcatcatc cagctaatgt agttagtggt   1080
tgattcgtca gcaatgacgt aaaacatttg tatcgatcct cactccttat ctataaaagg   1140
ttgagttatt tttcttggaa ggacatctcg aaactagcag tcctctcctt tcaaaaaatt   1200
tatcttttta agtttttagt cgtcgt                                        1226

<210> SEQ ID NO 2
<211> LENGTH: 1130
<212> TYPE: DNA
<213> ORGANISM: Lamium Leaf Distortion Associated Virus
<220> FEATURE:
<221> NAME/KEY: promoter
<222> LOCATION: (1)..(1130)
<223> OTHER INFORMATION: LLDAV TR1 Promoter Sequence

<400> SEQUENCE: 2
cgaatgttct acacaagaaa tacaaaggct tcatagaagc aagaacggcg gcagatttat     60
actgcaaaaa tcatgggtta gaacctctca agttctattc tgaagaagct actcttcaac    120
ccaagcagcc taaagaaaaa gttccatccg gcgaactacc cagctcttct ctcaagaag    180 ctgatacacc agatgtaaac attgtcatgg aagacttcat gaatgtctac aaggctgcaa    240
gagctcatta agatgaacga ttcttcatcg accacttctt caccaccgag aagaaaatc    300 taagcttttta caatttctgt gaatgttcag atcctgagat cgtaaaagat gcctatcttt    360
gtggattgat caaaacaatc tacccaggtc ctaatctctt ggagatttct ccttccta     420 aagagataag aagaaatgtc aagctattca gacgaaagtg cattaaagat ccaagtaaga    480
aaatttactt gaaattctcc agcactattc ccagatgggg aaagaaggt gaacaggttt     540 actggccaca tcaccatata actatgggtg ttcgttccga agaagaacaa taccagcctt    600
ccagacaaat ggaagcccaca cttgaggttc aagaccttga agaactagct gttcaaaaaa    660
ttcaacagtt catcgaaaag atgtttgaat tcagcaagga agattagact tttgtcaatc    720
ttatctggaa tagggttttg ataacttcaa aatctttcaa accactcagc acaagccatg    780
tggaattgat tcttcttttt caaaagaggt aaagaatca ttatgactttt ggaccccacc    840
```

| | |
|---|---|
| atccactcat atgcaaaagc atagagaaaa agtcagtgga atacagctgc ctcaactgta | 900 |
| gcaaaggcaa aaggccaaag aaagacggac acgtagaaga ttctgcgaca acgtcgtcat | 960 |
| catccagcta atgtagttag tggttgattc gtcagcaatg acgtaaaaca tttgtatcga | 1020 |
| tcctcactcc ttatctataa aaggttgagt tattttttctt ggaaggacat ctcgaaacta | 1080 |
| gcagtcctct cctttcaaaa aatttatctt tttaagtttt tagtcgtcgt | 1130 |

<210> SEQ ID NO 3
<211> LENGTH: 904
<212> TYPE: DNA
<213> ORGANISM: Lamium Leaf Distortion Associated Virus
<220> FEATURE:
<221> NAME/KEY: promoter
<222> LOCATION: (1)..(904)
<223> OTHER INFORMATION: LLDAV TR2 Promoter Sequence

<400> SEQUENCE: 3

| | |
|---|---|
| ctacaaggct gcaagagctc attaagatga acgattcttc atcgaccact tcttcaccac | 60 |
| cgagaagaaa aatctaagct tttacaattt ctgtgaatgt tcagatcctg agatcgtaaa | 120 |
| agatgcctat ctttgtggat tgatcaaaac aatctaccca ggtcctaatc tcttggagat | 180 |
| ttctctcctt cctaaagaga taagaagaaa tgtcaagcta ttcagacgaa agtgcattaa | 240 |
| agatccaagt aagaaaattt acttgaaatt ctccagcact attcccagat ggggaaaaga | 300 |
| aggtgaacag gtttactggc cacatcacca tataactatg ggtgttcgtt ccgaagaaga | 360 |
| acaataccag ccttccagac aaatggaagc cacacttgag gttcaagacc ttgaagaact | 420 |
| agctgttcaa aaaattcaac agttcatcga aagatgtttt gaattcagca aggaagatta | 480 |
| gacttttgtc aatcttatct ggaatagggt tttgataact tcaaaatctt tcaaaccact | 540 |
| cagcacaagc catgtggaat tgattcttct ttttcaaaag aggttaaaga atcattatga | 600 |
| ctttggaccc caccatccac tcatatgcaa aagcatagag aaaaagtcag tggaatacag | 660 |
| ctgcctcaac tgtagcaaag gcaaaaggcc aagaaagac ggacacgtag aagattctgc | 720 |
| gacaacgtcg tcatcatcca gctaatgtag ttagtggttg attcgtcagc aatgacgtaa | 780 |
| aacatttgta tcgatcctca ctccttatct ataaaaggtt gagttatttt tcttggaagg | 840 |
| acatctcgaa actagcagtc ctctcctttc aaaaaattta tcttttttaag tttttagtcg | 900 |
| tcgt | 904 |

<210> SEQ ID NO 4
<211> LENGTH: 885
<212> TYPE: DNA
<213> ORGANISM: Lamium Leaf Distortion Associated Virus
<220> FEATURE:
<221> NAME/KEY: promoter
<222> LOCATION: (1)..(885)
<223> OTHER INFORMATION: LLDAV TR3 Promter Sequence

<400> SEQUENCE: 4

| | |
|---|---|
| cattaagatg aacgattctt catcgaccac ttcttcacca ccgagaagaa aaatctaagc | 60 |
| ttttacaatt tctgtgaatg ttcagatcct gagatcgtaa aagatgccta tctttgtgga | 120 |
| ttgatcaaaa caatctaccc aggtcctaat ctcttggaga tttctctcct tcctaaagag | 180 |
| ataagaagaa atgtcaagct attcagacga agtgcatta aagatccaag taagaaaatt | 240 |
| tacttgaaat tctccagcac tattcccaga tggggaaaag aaggtgaaca ggtttactgg | 300 |
| ccacatcacc ataactatat gggtgttcgt tccgaagaag aacaatacca gccttccaga | 360 |
| caaatggaag ccacacttga ggttcaagac cttgaagaac tagctgttca aaaaattcaa | 420 |

```
cagttcatcg aaaagatgtt tgaattcagc aaggaagatt agactttgt caatcttatc      480 tggaataggg ttttgataac ttcaaaatct ttcaaaccac tcagcacaag ccatgtggaa     540
ttgattcttc tttttcaaaa gaggttaaag aatcattatg actttggacc ccaccatcca    600
ctcatatgca aaagcataga gaaaaagtca gtggaataca gctgcctcaa ctgtagcaaa    660
ggcaaaaggc caaagaaaga cggacacgta gaagattctg cgacaacgtc gtcatcatcc    720
agctaatgta gttagtggtt gattcgtcag caatgacgta aaacatttgt atcgatcctc    780
actccttatc tataaaaggt tgagttattt tcttggaag gacatctcga aactagcagt     840
cctctccttt caaaaatttt atcttttaa gttttagtc gtcgt                      885

<210> SEQ ID NO 5
<211> LENGTH: 443
<212> TYPE: DNA
<213> ORGANISM: Lamium Leaf Distortion Associated Virus
<220> FEATURE:
<221> NAME/KEY: promoter
<222> LOCATION: (1)..(443)
<223> OTHER INFORMATION: LLDAV TR4 Promoter Sequence

<400> SEQUENCE: 5
aattcagcaa ggaagattag acttttgtca atcttatctg gaatagggtt ttgataactt    60
caaaatcttt caaaccactc agcacaagcc atgtggaatt gattcttctt tttcaaaaga   120
ggttaaagaa tcattatgac tttggacccc accatccact catatgcaaa agcatagaga   180
aaaagtcagt ggaatacagc tgcctcaact gtagcaaagg caaaaggcca agaaagacg    240 gacacgtaga agattctgcg acaacgtcgt catcatccag ctaatgtagt tagtggttga   300
ttcgtcagca atgacgtaaa acatttgtat cgatcctcac tccttatcta taaaggttg    360 agttattttt cttggaagga catctcgaaa ctagcagtcc tctcctttca aaaatttat    420 cttttaagt ttttagtcgt cgt                                            443

<210> SEQ ID NO 6
<211> LENGTH: 113
<212> TYPE: DNA
<213> ORGANISM: Lamium Leaf Distortion Associated Virus

<400> SEQUENCE: 6
cgatcctcac tccttatcta taaaggttg agttattttt cttggaagga catctcgaaa    60
ctagcagtcc tctcctttca aaaatttat cttttaagt ttttagtcgt cgt            113
```